United States Patent
Sweitzer et al.

(10) Patent No.: US 10,912,573 B2
(45) Date of Patent: Feb. 9, 2021

(54) INTRAMEDULLARY CANAL REAMER

(71) Applicant: S. S. White Technologies, Inc., St. Petersburg, FL (US)

(72) Inventors: Zachary Robert Sweitzer, Basking Ridge, NJ (US); Rebecca Arwen Wenokor, Highland Park, NJ (US)

(73) Assignee: Shukla Medical, St. Petersburg, FL (US)

( * ) Notice: Subject to any disclaimer, the term of this patent is extended or adjusted under 35 U.S.C. 154(b) by 349 days.

(21) Appl. No.: 15/073,695

(22) Filed: Mar. 18, 2016

(65) Prior Publication Data
US 2016/0270797 A1 Sep. 22, 2016

Related U.S. Application Data

(60) Provisional application No. 62/135,810, filed on Mar. 20, 2015.

(51) Int. Cl.
*A61B 17/16* (2006.01)

(52) U.S. Cl.
CPC ........ *A61B 17/164* (2013.01); *A61B 17/1615* (2013.01); *A61B 17/1637* (2013.01); *A61B 17/1635* (2013.01)

(58) Field of Classification Search
CPC .............. A61B 17/1637; A61B 17/164; A61B 17/1655; A61B 17/1668
See application file for complete search history.

(56) References Cited

U.S. PATENT DOCUMENTS

| 4,559,936 | A | * | 12/1985 | Hill | A61B 90/92 606/179 |
|---|---|---|---|---|---|
| 5,171,313 | A | | 12/1992 | Salyer | |
| 5,190,548 | A | * | 3/1993 | Davis | A61B 17/1615 408/204 |
| 5,312,408 | A | * | 5/1994 | Brown | A61B 17/1637 408/201 |
| 5,954,671 | A | * | 9/1999 | O'Neill | A61B 17/1637 600/567 |

(Continued)

FOREIGN PATENT DOCUMENTS

WO 00/45714 A1 8/2000

OTHER PUBLICATIONS

Extended European Search Report issued in European Application No. 17161653.5 dated Aug. 25, 2017.

(Continued)

*Primary Examiner* — Matthew J Lawson
(74) *Attorney, Agent, or Firm* — Kim IP Law Group LLC

(57) ABSTRACT

A reamer used in orthopedic surgery that reams and collects bone cement. The reamer may come in different diameters and is used when removal of bone cement is necessary, as is commonly done in revision surgeries. The reamer has a cutting tip with a fluted opening connected to a hollow body in which the bone cement chips or shavings collect after passing through the tip. The other end of the reamer has a hub that can connect to a drill. As the reamer advances into the IM canal it shaves the bone cement off of the walls and/or the bottom of the intramedullary canal. The reamer has a central channel extending throughout its length through which a guide wire may be placed.

20 Claims, 8 Drawing Sheets

SECTION A-A

(56) References Cited

U.S. PATENT DOCUMENTS

Figure 1D:
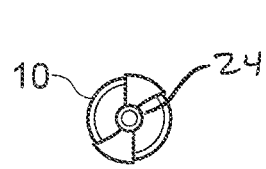

| | | | |
|---|---|---|---|
| 6,783,533 B2* | 8/2004 | Green | A61B 17/1617 606/80 |
| 6,890,336 B2 | 5/2005 | Nordman | |
| 7,611,515 B2 | 11/2009 | Wolford | |
| 7,632,275 B2 | 12/2009 | Williams | |
| 8,449,546 B2* | 5/2013 | Ries | A61B 17/1671 606/80 |
| 9,084,614 B2 | 7/2015 | Malawer | |
| 9,757,135 B1* | 9/2017 | Kelley | A61B 17/1637 |
| 9,901,355 B2* | 2/2018 | Bourque | A61B 17/1637 |
| 2003/0163136 A1 | 8/2003 | Joist | |
| 2006/0247552 A1* | 11/2006 | Ikehara | A61B 10/0096 600/562 |
| 2007/0123892 A1* | 5/2007 | Ries | A61B 17/1671 606/80 |
| 2007/0123909 A1* | 5/2007 | Rupp | A61B 17/92 606/104 |
| 2008/0195103 A1 | 8/2008 | Lawis et al. | |
| 2010/0063507 A1 | 3/2010 | Sidebotham et al. | |
| 2010/0094361 A1* | 4/2010 | Meneghini | A61B 17/1631 606/86 R |
| 2011/0144649 A1* | 6/2011 | Victor | A61B 17/1617 606/80 |
| 2011/0218575 A1* | 9/2011 | Culbert | A61B 17/1757 606/279 |
| 2012/0165832 A1* | 6/2012 | Oostman, Jr. | A61B 10/0266 606/131 |
| 2015/0342756 A1* | 12/2015 | Bays | A61F 2/4644 604/22 |

OTHER PUBLICATIONS

Supplemental Office Action issued in European Application No. 17161653.5 dated Nov. 8, 2019.

* cited by examiner

FIG. 1B    SECTION A-A

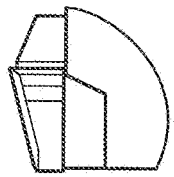
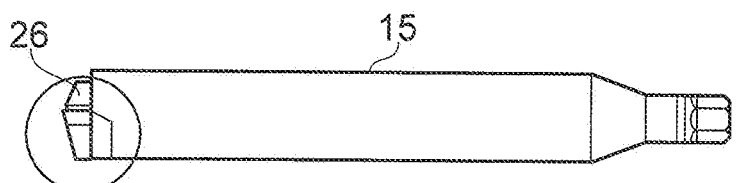
FIG. 2F  FIG. 2A
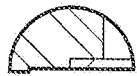
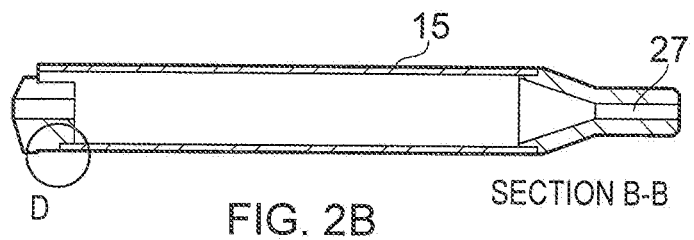
FIG. 2G  FIG. 2B  SECTION B-B
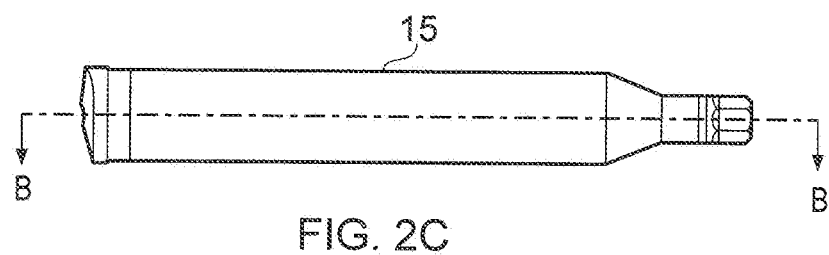
FIG. 2D  FIG. 2C
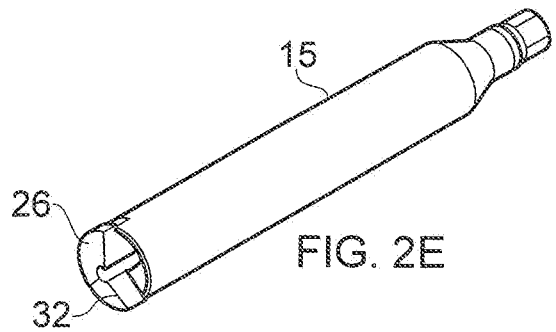
FIG. 2E

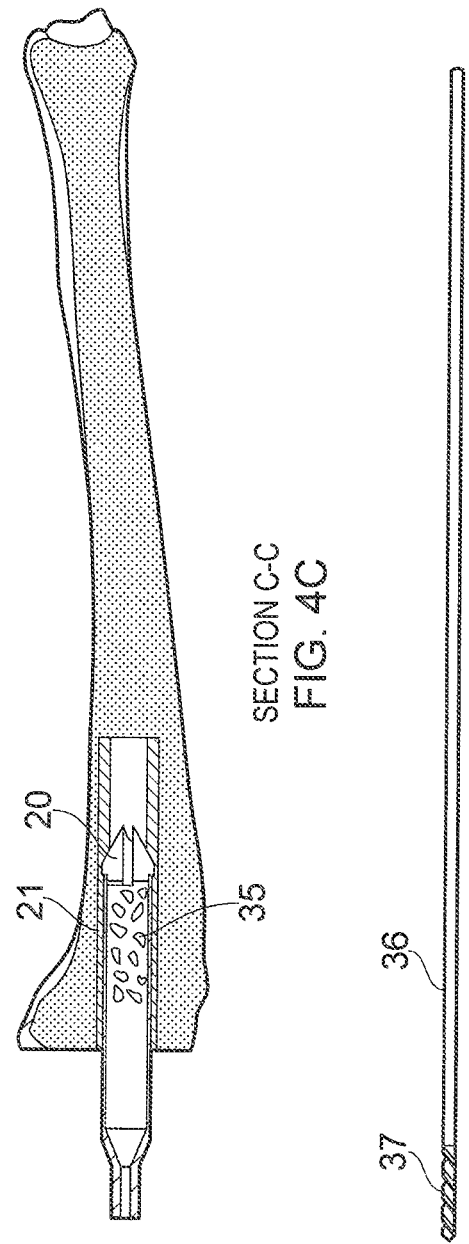
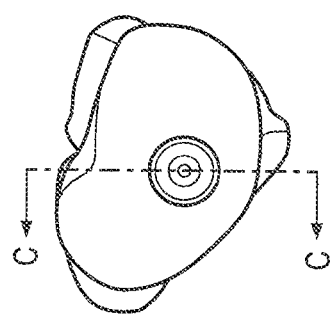
FIG. 4B
SECTION C-C
FIG. 4C
FIG. 5A

SECTION D-D         SECTION E-E

INTRAMEDULLARY CANAL REAMER

CROSS-REFERENCE TO RELATED APPLICATION

This application claims the benefit of U.S. Provisional Application Ser. No. 62/135,810 filed Mar. 20, 2015 and entitled Intramedullary Canal Reamer.

BACKGROUND OF THE INVENTION

This invention relates to a reaming tool for clearing an intramedullary canal, and more particularly for removing bone cement from it.

During orthopedic revision surgery it is common for existing orthopedic implants to be removed. Many of these implants have a stem which is cemented into the intramedullary ("IM") canal in the center of the bone. After the implant is extracted, bone cement usually lines the IM canal. Sometimes cement forms a plug at the bottom of the canal. Before inserting a new implant the operating surgeon must remove this residual cement.

Many of the current procedures for doing so are time consuming and tedious. They involve scraping, chiseling, ultra-sonic removal, or drilling the cement. Current devices do not exist that facilitate quick removal of the bone cement.

An object of the present invention is to provide a tool which can more efficiently remove material such as bone cement from an IM canal, than can prior art devices and methods.

SUMMARY OF THE INVENTION

As herein described, according to a first embodiment of the invention an intramedullary canal reamer has a substantially hollow cylindrical body and a conical head which incorporates a cutting blade. The head has an opening to permit bone cement or other removed material shavings to pass into and be contained within the reamer body. The outer diameter of the cylindrical body is less than the outer diameter of the path of rotation of a cutting edge of the cutting blade.

According to a second embodiment, the head of the reamer is substantially flat instead of conical, so as to be able to remove any cement or other plug at the bottom of the IM canal.

IN THE DRAWING

Figure 1A:
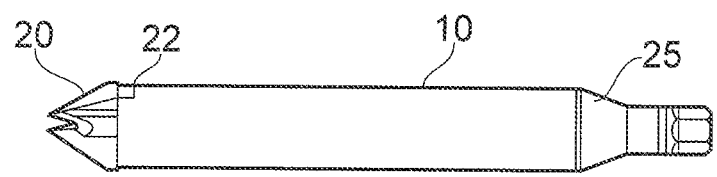
Figure 1G:
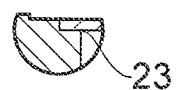
Figure 1F:
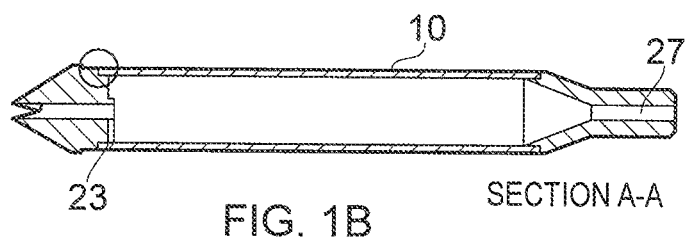
Figure 1F:
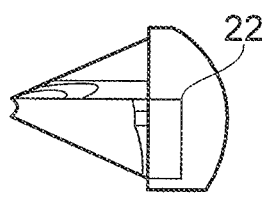
Figure 1C:
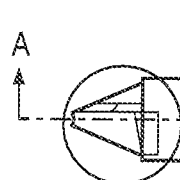
Figure 1E:
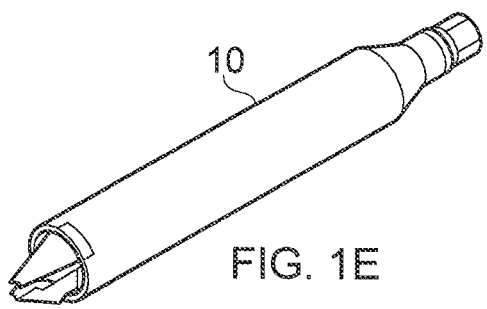
Figure 3A:
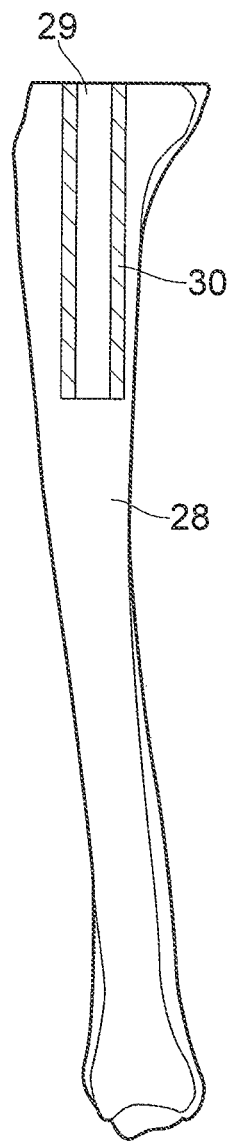
Figure 3B:
Figure 4A:
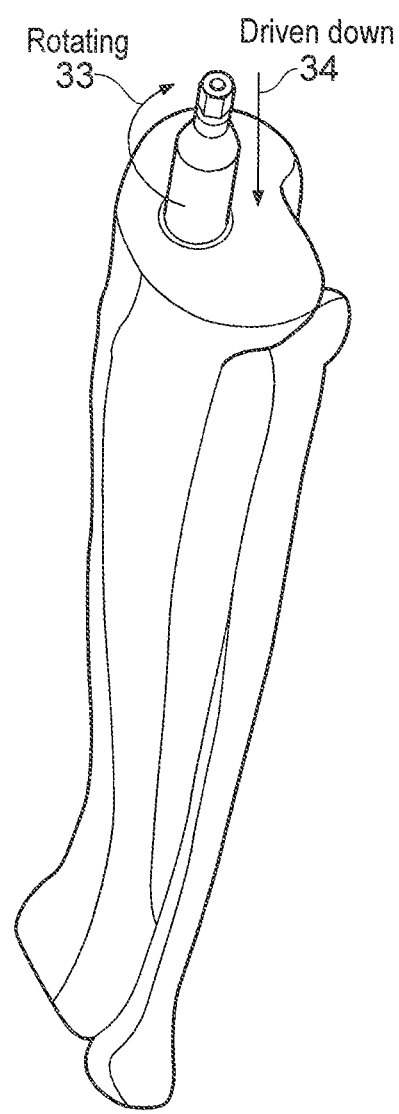
Figure 5B:
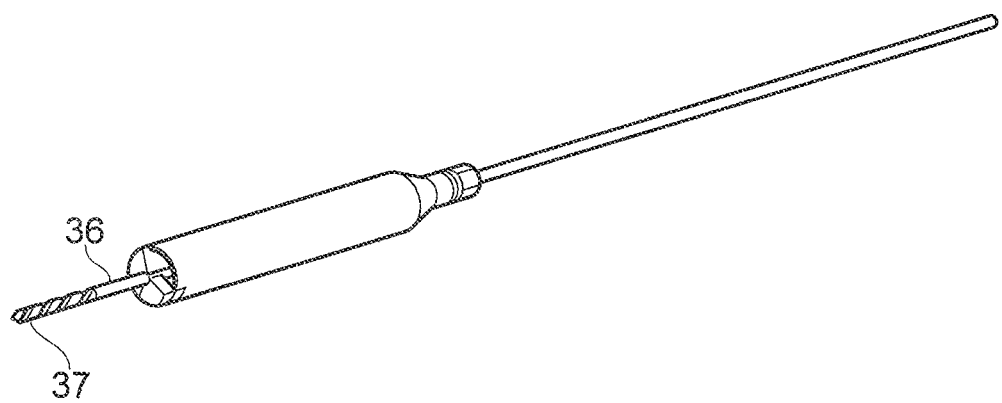
Figure 5C:
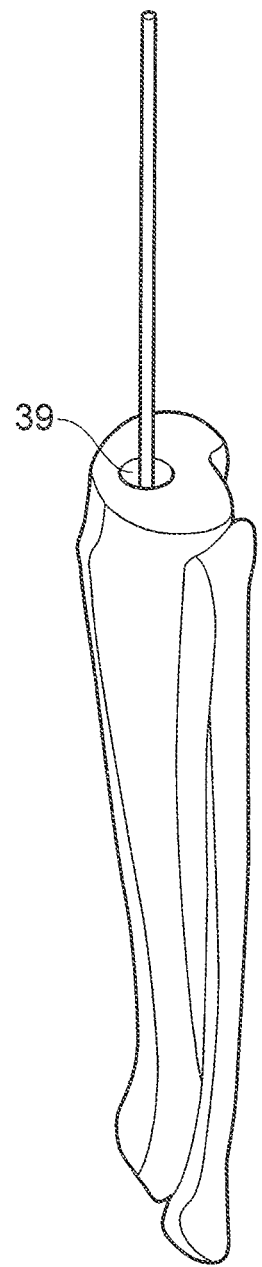
Figures 5D, 5E, 5F, 5G:
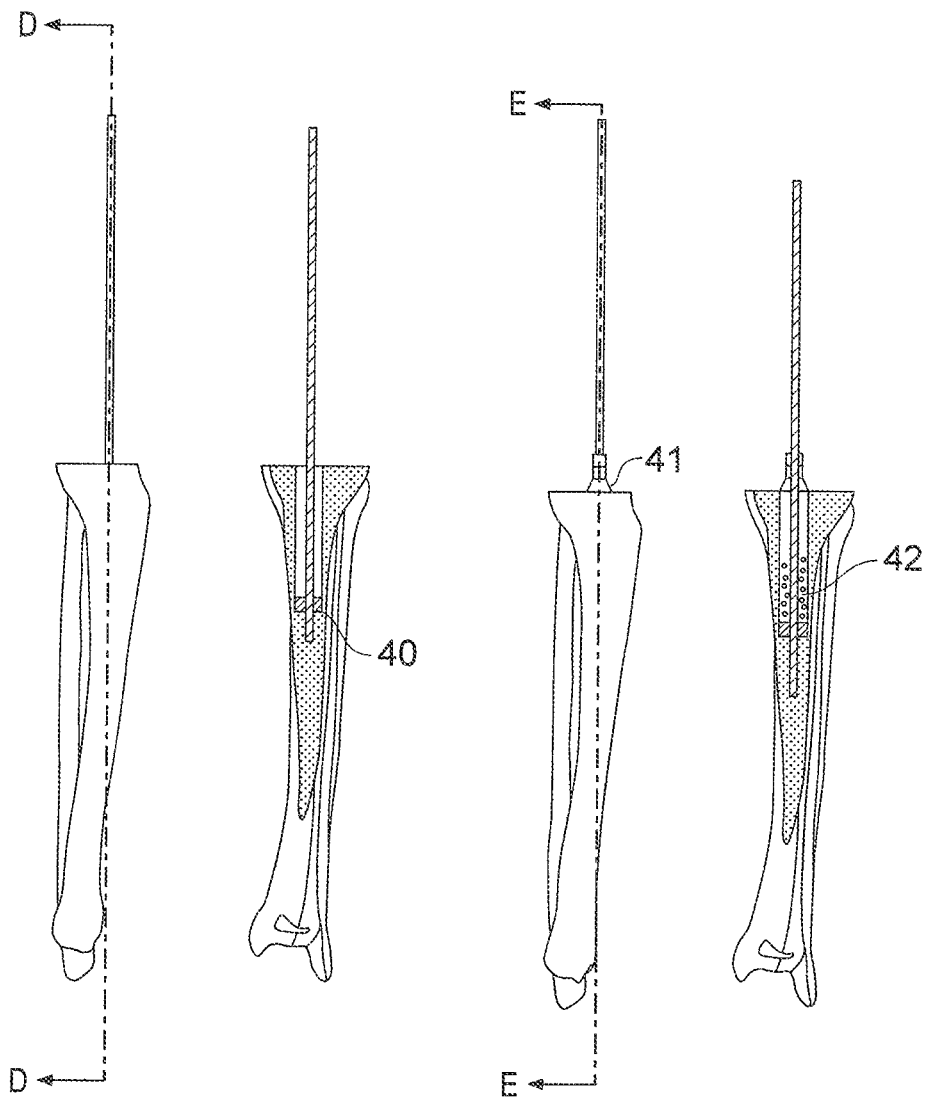

FIGS. 1A to 1G show a first embodiment of the invention, having a conical reaming head, wherein:
FIG. 1A is a right side elevation view thereof;
FIG. 1B is a right side cross-sectional view taken along the cutting plane A-A shown in FIG. 1A;
FIG. 1C is a top plan view thereof;
FIG. 1D is a front elevation view thereof;
FIG. 1E is an isometric view thereof;
FIG. 1F is a detail view of the mechanical interlock thereof; and
FIG. 1G is a detail view of the press-fit joint thereof.
FIGS. 2A to 2G show a second embodiment of the invention, having a substantially flat reaming head, wherein:
FIG. 2A is a right side elevation view thereof;
FIG. 2B is a right side cross-sectional view taken along the cutting plane B-B shown in FIG. 2A;
FIG. 2C is a top plan view thereof;
FIG. 2D is a front elevation view thereof;
FIG. 2E is an isometric view thereof;
FIG. 2F is a detail view of the mechanical interlock thereof; and
FIG. 2G is a detail view of the press-fit joint thereof.
FIG. 3A is a partial cross-sectional elevation view of a bone such as a tibia after an orthopedic implant has been extracted from its superior surface, leaving an IM canal with a bone cement lining on the canal walls.
FIG. 3B is a partial cross-sectional elevation view of a bone such as a tibia after an orthopedic implant has been extracted from its superior surface, leaving an IM canal with a bone cement plug at the bottom of the canal.
FIG. 4A is an isometric view of the bone shown in FIG. 3A, showing the reamer of either embodiment of the invention in the process of removing bone cement from the IM canal.
FIG. 4B is a top plan view of the bone and reamer shown in FIG. 4A.
FIG. 4C is a side cross-sectional view of the bone shown in FIGS. 4A and 4B taken along the cutting plane C-C shown in FIG. 4B.
FIG. 5A shows a guide wire with a drill head for engaging an axial channel in the reamer of either embodiment to keep the longitudinal axis of the reamer aligned with the longitudinal axis of the IM canal.
FIG. 5B is an isometric view of the reamer of FIGS. 2A to 2E with the guide wire extending through the axial channel thereof.
FIG. 5C is an isometric view of the bone shown in FIGS. 3A and 3B with the drill head of the guide wire engaging the center of the bottom of the IM canal, in preparation for placement of the reamer in position for removing bone cement.
FIG. 5D is another isometric view of the bone shown in FIG. 3B.
FIG. 5E is a partial cross-sectional elevation view of the bone shown in FIG. 5D, taken along the cutting plane D-D, with the guide wire engaging the center of the bottom of the IM canal, in preparation for placement of the reamer of FIGS. 2A to 2E in position for removing a bone cement plug at the bottom of the IM canal.
FIG. 5F is another isometric view of the bone shown in FIG. 3A.
FIG. 5G is a partial cross-sectional elevation view of the bone shown in FIG. 5F, taken along the cutting plane E-E, with the guide wire engaging the center of the bottom of the IM canal, in preparation for placement of the reamer of FIGS. 1A to 1E in position for removing a bone cement lining on the walls of the IM canal.

GENERAL DESCRIPTION

After the implant stem has been removed, the reamer is positioned with its head engaging the hole in the end of the IM canal, and rotated at low speed with a hand or electric drill, the opposite end of the reamer being held by the drill chuck. A reamer with a conical head or tip is used to remove bone cement from the walls of the IM canal, while a reamer with a flat head or tip is preferably used to remove a bone cement plug from the bottom of the canal, but may also be used to remove bone cement from the canal wall.

As either embodiment of the reamer spins, the cutting edge of the blade comprising its tip shaves bone cement and advances into the IM canal; with the resulting bone cement shavings being collected inside the cylindrical body of the reamer.

The reamer preferably has a smooth outside surface so as to minimize any milling of adjacent bone.

For the reamer of FIGS. 1A to 1E, the cutting blade comprising the conical tip is oriented at a low angle to the reamer longitudinal axis, preferably in the range of 15° to 30°; which is optimal for reaming the bone cement while keeping the reamer centered inside the IM canal.

It is preferable to initially use a reamer with a diameter significantly less than that of the IM canal. After the first reaming pass, a similar reamer with a greater diameter which is still less than that of the canal is used. This procedure minimizes any risk of damaging bone adjacent the IM canal. Depending on the size of the canal and the thickness of the cement, more than two passes may be made, with reamers of successively increasing diameter.

When there is only a very thin layer of bone cement left attached to the surface of the IM canal, that thin layer can be easily removed by conventional means such as a retrograde chisel.

When used with an electric drill, the reamer connects to the surgical drill via a quick connect coupling. With the drill set to slow or "ream" speed, the surgeon directs the reamer into the IM canal and moves it further into the canal as the reamer cuts away bone cement.

The reamer of FIGS. 1A to 1E or FIGS. 2A to 2E is preferably provided with an axial channel, i.e. cannulated, so as to accommodate a guide wire to help keep the reamer aligned with the longitudinal axis of the IM canal, with the guide wire passing through the reamer cannula or channel.

If the reamer is used freehand, the rigidity of the connection between the reamer to and drill helps the surgeon to keep the reamer aligned with the central axis of the IM canal.

When the reamer is withdrawn from the IM canal, with its tubular interior containing collected bone cement chips and debris, the reamer can be discarded. Alternatively, the reamer may be constructed so that the head is readily removable and replaceable, permitting the reamer body to be emptied and reused.

The outer diameter of the tubular portion of the reamer is slightly smaller than the outer diameter of the path of rotation of the cutting blade. This reduces rubbing of the exterior of the reamer body against the inside wall of the hole during reaming and thus reduces heat due to friction, so that the cement comprising the wall does not heat up and/or melt and could then cool to lock the reamer in place if it stops spinning.

If the hole in the IM canal which is left when the implant is removed (the "extraction cavity") is off center in relation to the longitudinal axis of the IM canal, then the reamer axis should preferably be aligned with the IM canal and not the extraction cavity. In order to do this a handle with a plastic bearing loop can be slid over the tube of the reamer and a side force can be applied to the reamer. This will cause the cutting blade of the reamer to side mill the cement, allowing the reamer to align with the IM canal axis. This arrangement can be used instead of, or preferably with a guide wire as hereafter described.

DETAILED DESCRIPTION

The reamer 10 shown in FIG. 1A has a conical cutting head, tip or bit 20 that is connected to a cylindrical or tubular body 21 by a mechanical interlock 22 and a press fit joint 23. The press fit joint is created by the outer dimension of the bit 20 and the inner dimension of the tube 21 in this region being such that the two pieces must be pressed together. The mechanical interlock is such that there is a slot and key fit between the tip 20 and the tube 21. Once these two pieces are pressed together, the contiguous edges (shown in detail in FIG. 1F) are laser welded.

This arrangement provides adequate connection strength to resist the torque applied between the head and body during use, and prevents the bit from breaking off from the tube if, for example, the bit encounters a metal object in the IM canal such as a broken screw. The conical cutting tip 20 has flutes 24 (FIG. 1D) that allow bone cement shavings to pass through the tip into the interior of the reamer body 21.

The tube 21 is connected to the drill coupling or hub 25 via the same means (mechanical interlock and press fit) as the cutting bit is connected to the tube. The hub may be a hexagonal or other noncircular geometrical shape that allows a non-slip connection for application of torque. The torque or rotational power may be provided by a power drill or a hand drill.

In FIGS. 2A through 2G, the reamer 15 has, instead of a conical tip, a substantially flat cutting tip 26. The diameter of either configuration may vary and multiple sizes may be used during operation to gradually increase the diameter of the bore in the IM Canal to sequentially remove layers of bone cement until reaching the wall of the canal itself.

Either the conical tip (FIGS. 1A to 1G) or flat tip (FIGS. 2A to 2G) configuration may be provided with an axial channel or cannula 27 having a relatively small diameter (compared to the tube diameter) extending through the entire length of the reamer.

FIG. 3A shows a cross section of a tibia bone 28 including the cylindrical recess 29 where an implant stem from a prior surgery had resided, leaving a cement layer 30 adherent the wall of the IM Canal. To remove that wall, the conical tip reamer is preferred, as the conical shape of the bit keeps the reamer centered in the IM canal and the angle of the bit helps to smoothly shave the cement off the canal wall as opposed to ripping chunks of cement off the wall.

FIG. 3B shows a tibia bone with a residual plug 31 of bone cement below where the implant stem had resided. To remove this plug, the flat tip reamer 15 is preferred. The flat shape of the bit 26 engages the cement plug more efficiently than does the conical bit, because the point of the conical bit would machine deeper into the IM canal than is necessary to remove all of the cement, and thus remove bone that should be retained.

The shape of the cutting edge 32 of the flat tip bit 26 reduces the risk of clogging with cement because of its cutting edge 32.

As shown in FIG. 4A, each reamer is operated by slowly rotating it about the corresponding longitudinal axis as indicated by arrow 33, while gradually urging the reamer into the IM canal as indicated by the arrow 34.

The reamers may have depth markings on the outside of the hollow tube so the user can see how much farther the reamer needs to be advanced into the IM canal. As the reamer advances, the cutting tip 20 of the reamer 10, for example, shaves the bone cement and the fragments or shavings 35 pass through the fluted opening of the corresponding bit and are collected inside the hollow tube 21.

After a successful pass, the reamer can be withdrawn from the IM canal and discarded with the bone cement fragments inside the reamer tube. If there is more bone cement left in the canal that now is a larger effective diameter than the cutting path of the reamer, a larger diameter reamer can be used.

In cases where it proves difficult to keep the reamer centered in the IM canal, a guide wire 36 can be used. This guide wire is a solid shaft typically of metal, with a drill bit tip 37 as shown in FIG. 5A.

Since each reamer is fully cannulated, that is, has an axial channel extending throughout its length, the reamer can slide freely over the length of the guide wire 36. There should be a close sliding fit between the exterior of the guide wire and the interior of the channel it is situated in, so as to guide the reamer without significant play.

If the surgeon decides to use the guide wire, a drill will be used to drive the guide wire down into the center of the bottom of the IM canal as shown by the guide wire position 39 in FIG. 5C. With the drill tip positioned concentrically with the guide wire, the wire can be drilled into the bottom of the cavity 40 (FIG. 5E) to anchor the guide wire in place. Then, as shown by the numeral 41 in FIG. 5F, the reamer is slid over the free end of the wire and into the IM canal to shave the bone cement and collect it inside of the hollow reamer tube 42 (FIG. 5G).

The surgical drills or handles used with these reamers are generally cannulated as well, so that the guide wire may pass through the entire assembly.

We claim:

1. An intramedullary canal reamer having:
   a reamer body that includes a substantially annular hollow body; and
   a cutting head consisting essentially of:
      a cylindrical base mounted within the substantially annular hollow body for plugging a distal end of the substantially annular hollow body,
      a fluted opening extending through the cylindrical base to permit bone cement or other removed material shavings to pass into and be contained within the reamer body,
      wherein the cylindrical base includes a substantially planar backend within the annular hollow body defining a floor having a proximally facing surface area larger than a cross-sectional area of the fluted opening at a proximally facing surface of the floor, and
      first and second substantially pyramidal-shaped cutting inserts spaced apart and diametrically opposed, and extending from the base,
      wherein a revolution of the first and second substantially pyramidal-shaped cutting inserts along a longitudinal central axis of the cutting head forms a substantially conical profile, and
      wherein each of the first and second substantially pyramidal-shaped cutting inserts includes a distally directed cutting edge that converges from its proximal end to its distal end.

2. The reamer according to claim 1, further comprising a drill adapter coupling affixed to an end of the reamer remote from the head thereof.

3. The reamer according to claim 1, wherein the head is connected to the reamer body by a mechanical interlock.

4. The reamer according to claim 1, wherein the cutting head is connected to the reamer body by a mechanical interlock comprising a slot and key fit between the head and the reamer body.

5. The reamer according to claim 1, wherein the cutting head is in press fit connection with the reamer body.

6. The reamer according to claim 1, wherein the floor extends perpendicular to the substantially annular hollow body.

7. The reamer according to claim 1, wherein an internal diameter of the opening of the cutting head is less than one half the internal diameter of the reamer body.

8. The reamer according to claim 1, wherein a portion of the cutting head has an overall width less than an overall width of the reamer body.

9. The reamer according to claim 1, wherein a portion of the cutting head has an overall width greater than an overall width of the reamer body.

10. The reamer according to claim 1, wherein the cylindrical base is press-fitted into the substantially annular hollow body.

11. An intramedullary canal reamer having:
    a reamer body that includes an annular body; and
    a head comprising:
       a cylindrical base mounted within the annular body for plugging a distal end of the annular body,
       a fluted opening extending through the cylindrical base and in fluid communication with the reamer body,
       wherein the cylindrical base includes a substantially planar backend within the annular body defining a floor having a proximally facing surface area larger than a cross-sectional area of the fluted opening at a proximally facing surface of the floor, and
       first and second cutting inserts circumferentially spaced apart and diametrically opposed, each extending from the base and having a cutting blade,
       wherein the first and second cutting inserts have a first overall width that is greater than an overall width of the reamer body, and a second overall width perpendicular to the first overall width that is less than the overall width of the reamer body.

12. The reamer according to claim 11, wherein the head is substantially flat.

13. The reamer according to claim 11, wherein the fluted opening is sized sufficiently to permit bone cement or other removed material shavings to pass through or be sufficiently contained within the reamer body.

14. The reamer according to claim 11, wherein the cylindrical base forms a seal coextensive with the annular body.

15. The reamer according to claim 11, further comprising a drill adapter coupling affixed to an end of the reamer remote from the head thereof.

16. An intramedullary canal reamer having:
    a reamer body that includes a substantially hollow cylindrical body;
    a head consisting essentially of:
       a cylindrical base, and
       an opening extending through the head, the opening comprising at least one flute to permit bone cement or other removed material shavings to pass into and be contained within the reamer body, and
       first and second cutting inserts spaced apart and diametrically opposed to allow the removed material shavings to pass through the flute and into the reamer body,
       wherein a revolution of the first and second cutting inserts along a longitudinal central axis of the cutting head forms a substantially conical profile, and
       wherein the cylindrical base includes a substantially planar backend within the substantially hollow body defining a floor having a proximally facing surface area larger than a cross-sectional area of the opening at a proximally facing surface of the floor; and
    a coupling affixed to an end of the reamer remote from the head thereof.

17. The reamer according to claim 16, wherein the cylindrical base forms a seal coextensive with the substantially hollow cylindrical body.

18. The reamer according to claim 16, wherein the coupling is a drill coupling.

19. The reamer according to claim 16, wherein the head is connected to the reamer body by a mechanical interlock.

20. The reamer according to claim 16, wherein the cylindrical base is press-fitted into the substantially hollow cylindrical body.

\* \* \* \* \*